United States Patent [19]
Hunter et al.

[11] Patent Number: 5,092,901
[45] Date of Patent: Mar. 3, 1992

[54] SHAPE MEMORY ALLOY FIBERS HAVING RAPID TWITCH RESPONSE

[75] Inventors: Ian Hunter; Serge R. Lafontaine, both of Montreal, Canada

[73] Assignee: The Royal Institution for the Advancement of Learning (McGill University), Montreal, Canada

[21] Appl. No.: 534,131

[22] Filed: Jun. 6, 1990

[51] Int. Cl.$^5$ .......................... A61F 2/70; A61F 2/08
[52] U.S. Cl. ........................................ 623/24; 623/14; 60/528; 901/21
[58] Field of Search .................. 623/14, 24, 25, 63–65, 623/58; 60/528, 527; 901/21, 28, 25, 39

[56] References Cited

U.S. PATENT DOCUMENTS

| | | | |
|---|---|---|---|
| 3,827,426 | 8/1974 | Page et al. | 600/16 X |
| 3,858,141 | 12/1974 | Lackey | 219/492 X |
| 4,503,569 | 3/1985 | Dotter | 604/8 X |
| 4,556,050 | 12/1985 | Hodgson et al. | 600/30 |
| 4,655,489 | 2/1987 | Krumme et al. | 604/245 |
| 4,700,541 | 10/1987 | Gabriel et al. | 60/528 |
| 4,715,637 | 12/1987 | Hosoda et al. | 901/30 X |
| 4,716,731 | 1/1988 | Sakai et al. | 60/527 |
| 4,838,859 | 6/1989 | Strassman | 604/95 |

FOREIGN PATENT DOCUMENTS

| | | | |
|---|---|---|---|
| 0084427 | 4/1986 | Japan | 901/28 |
| 1240574 | 6/1986 | U.S.S.R. | 901/21 |
| 1271738 | 11/1986 | U.S.S.R. | 901/25 |
| 1278198 | 12/1986 | U.S.S.R. | 901/21 |
| 1313699 | 5/1987 | U.S.S.R. | 901/39 |

*Primary Examiner*—Randall L. Green
*Assistant Examiner*—David H. Willse
*Attorney, Agent, or Firm*—Bachman & LaPointe

[57] ABSTRACT

A modified shape memory alloy fibers exhibits a rapid twitch response under stimulation by an action potential such as the heating effect of an electromagnetic pulse; in particular the relaxation time of the twitch response is considerably shortened as compared with that of the unmodified fibers; the modification is achieved by simultaneous application of a stretching force and a short, powerful electromagnetic pulse effective to bring about contraction resulting from the shape memory and change material properties; this application is carried out a plurality of times.

23 Claims, 2 Drawing Sheets

SHAPE MEMORY ALLOY FIBERS HAVING RAPID TWITCH RESPONSE

BACKGROUND OF THE INVENTION i) Field of the Invention

This invention relates to modified elongate a fibers of a shape memory alloy, their preparation and use as actuation elements for generation of a working force.

ii) Description of Prior Art

Metal alloys are known which exhibit a shape memory effect. Such alloys exhibit a thermoelastic behavior resulting from transportation from a parent phase stable at an elevated temperature to a martensite phase at a lower temperature. If the alloy is deformed to a first particular shape while in the parent phase and is then shape adjusted while in the martensite phase to a second shape, the first shape is restored when the alloy is heated to the temperature at which transformation from the martensite phase to the parent phase occurs.

In considering the use of shape memory alloys in robotics and prosthesis, it is instructive to compare the properties of shape memory alloys with those of skeletal muscles and the ubiquitous electromagnetic actuators.

In a skeletal muscle of a mammal the tension or maximum force generated per unit cross-sectional area is a substantially constant 350 $kN/m^2$. In comparison the maximum substainable force generated by commercial high performance linear electromagnetic motors is more than 100 times less. Thus a Bruel & Kjaer linear motor (Model B & K 4810) generates a maximum tension of 2.6 $kN/m^2$. A short muscle having a muscle length which is the same as the muscle diameter can generate a force per unit mass of about 310 N/kg, whereas Model B & K 4810 generates only 9 N/kg. Muscle usually shortens by more than 20% in a limb, whereas Model B & K 4810 shortens by a maximum of 8%.

A skeletal muscle comprises a bundle of muscle fibers, generally in parallel relationship. More powerful muscles have more fibers, and muscles that must shorten over considerable distances have longer muscle fibers.

Robot limbs have been constructed using elongate Ni-Ti shape memory fibers. A Ni-Ti shape memory fiber having a diameter of 0.8 mm will generate over 100 $MN/m^2$ tension and shorten by up to 10% of its length. These shape memory fibers suffer a major drawback in that the total contraction and relaxation time is unduly slow and in particular the relaxation time is unduly slow. These shape memory fibers have a total contraction and relaxation time slower than both muscle and most electromagnetic actuators.

SUMMARY OF THE INVENTION

It is an object of this invention to provide an elongate fiber of a shape memory alloy of modified character.

It is a further object of this invention to provide an elongate fiber of shape memory alloy having a short total contraction and relaxation time.

It is a still further object of this invention to provide a method of producing modified elongate fibers of a shape memory alloy.

It is yet another object of this invention to provide an actuator element for generation of a working force, in the form of a modified elongate fiber of a shape memory alloy.

It is a still further object of this invention to provide a motor unit for generation of a working force based on at least one actuator element of the invention.

It has now been found that subjecting an elongate fiber of a shape memory alloy simultaneously to a stretching force and a short, powerful electromagnetic pulse effective to cause contraction of the fiber length and change material properties, results in a modification of the shape memory parameters of the fiber; more especially the modified fiber has a total contraction and relaxation time much shorter than that of the unmodified fiber.

In particular the relaxation time of the modified fiber is much shorter than that of the corresponding unmodified fiber, with the result that the fiber exhibits a rapid twitch response under stimulation by a current pulse (an action potential).

The modified elongate fibers may function as an artificial muscle-like actuator element for generation of a working force in robotics or prosthetics and may form part of a motor unit for generation of a working force in robotics or prosthetics.

DESCRIPTION OF PREFERRED EMBODIMENTS a) Elongate Fiber

The unmodified elongate fiber employed to produce the modified fiber of the invention is formed from a shape memory metal alloy.

The most widely employed fibers of this type are the Ni-Ti fibers available under the Trade Mark Nitinol. The phase transformation temperatures which are a characteristic of the shape memory are well established and are dependent on the relative proportions of the alloying elements Ni and Ti and the optional inclusion of alloying additives.

Other shape memory alloys include Ag-Cd, Au-Cd, Au-Cu-Zn, Cu-Al, Cu-Al-N, Cu-Zn, Cu-Zn-Al, Cu-Zn-Ga, Cu-Zn-Si, Cu-Zn-Sn, Fe-Pt, Fe-Ni, In-Cd, In-Ti, Ti-Nb and Ti-Ni.

Commercially available fibers typically have a diameter of 0.01 to 10 mm, usually 0.025 to 1 mm, usually greater than 0.1 mm. The length depends on the application.

Ni-Ti fibers are preferred fibers of the invention.

The unmodified fibers typically have a total contraction and relaxation time in excess of 1000 ms for a 0.8 mm diameter fiber. Typically the contraction time is not more than about 50 ms, and the relaxation time is in excess of 950 ms for a 0.8 mm diameter fiber.

b) Modification

The elongate fibers are modified to produce modified fiber exhibiting a change in material properties by the simultaneous application of a stretching force and a short, powerful, electromagnetic pulse.

In order to achieve this the fiber is suitably connected at one end to a linear electromagnetic motor and at the other end to a force transducer. The motor applies a moderate, linear stretching tension (i.e., force/unit cross-sectional area of the fibers), for example, of the order of 40 $MN/m^2$. A short, very powerful electric potential is applied across the ends of the fiber to produce an electromagnetic pulse effective to achieve a contraction in length of the fiber, while the linear stretching force is maintained.

Suitably this electromagnetic pulse has a current density of 400 to 4000 MA/m$^2$ and is of short duration so as not to destroy the integrity of the fibers.

In the case of a pulse of 400 MA/m$^2$ the duration of the pulse is suitably not more than 5 ms, whereas in the case of a 4000 MA/m$^2$ pulse the duration is suitably not more than 0.5 ms.

For a 0.8 mm diameter fiber, suitably about 75 to 125, preferably about 100 electromagnetic pulses are applied, and the pulses are required to have a high rate of change of current. Thus for a 0.8 mm diameter fiber a rate of change of current of 10,000 A/sec. does not produce a satisfactory modified fiber, whereas a rate of change of current of 200,000 A/sec. does. An optimum rate of change of current in the pulse is 10$^6$ A/sec.

The modification may conveniently be carried out in a cooling environment to cool the fibre following the temperature increase associated with each pulse. For this purpose the modification is conveniently carried out with the fiber immersed in a bath of liquid coolant, for example, 50% methanol/50% water at $-20°$ C.

c) Modified Fibers

The modified shape memory alloy fibers of the invention exhibit a rapid twitch response under stimulation by an action potential, the twitch being the contraction and relaxation exhibited by the modified elongate fiber in response to the stimulation.

The action potential which serves as stimulation may suitably take the form of a brief current pulse of fixed amplitude and duration, for example, for a 0.8 mm diameter fiber, a pulse of about 50 A for a 1 ms duration. The pulse heats the fiber causing rapid contraction to the memory state which contraction is followed by a rapid relaxation.

The modified fibers more particularly have for a 0.8 mm diameter fiber a twitch response of less than 40 ms, of which the contraction rise time is not more than 10 ms and the relaxation decay time is about 60% completed in 15 ms.

Applications

The modified fibers of the invention find use in applications in which they function as actuator elements for generation of a working force.

Thus the fibers may be employed in motor units to simulate an artificial muscle in robotics or prosthetics.

Such an artificial muscle would consist of a number of motor units arranged in parallel. The number of motor units employed is a function of the total force required by the artificial muscle. The more motor units employed, the greater the total force produce.

Each motor unit may comprise a bundle of discrete elongate modified fibers in side-by-side parallel relationship and electrically insulated from each other along their length. In this case the fibers are electrically in parallel relationship. Alternatively a motor unit may comprise a single elongate modified fiber arranged in a sinusoidal-like path to provide lengths of the fiber in side-by-side parallel relationship; the side-by-side lengths being electrically insulated from each other. In this case the lengths of fiber are electrically in series relationship.

A motor unit containing a bundle of modified fibers may typically contain 5 to 15, more usually 10 fibers. The fibers of different motor units of an artificial muscle may be stimulated independently by separate pulses or pulse sources, more especially sequentially. In this way it is possible to operate the unit while avoiding restimulation of a stimulated fiber which has not completed the relaxation phase; and the working force is generated by a combination of rate and recruitment.

Re-stimulation of a plurality of stimulated fibers during the relaxation phase results in a non-linear summation of the generated forces producing a saturated or constant force level termed the tetanic force.

A pair of artificial muscles each comprising a collection of motor units in parallel may be arranged as an agonist-antagonistic pair which act in opposition but not simultaneously; in this way a working force may be generated by contraction of the fibers of one artificial muscle of the pair for work in one direction, followed by work in the other direction by the other artificial muscle; the agonist-antagonist pair can also be stimulated simultaneously to produce a stiffening effect.

If increased working force is required this can be achieved by employing more fibers, i.e., recruitment, or by stimulating the fibers more rapidly.

BRIEF DESCRIPTION OF DRAWINGS

The invention is further illustrated and explained by reference to the accompanying drawings, in which.

DESCRIPTION WITH REFERENCE TO THE DRAWINGS

Figure 1:
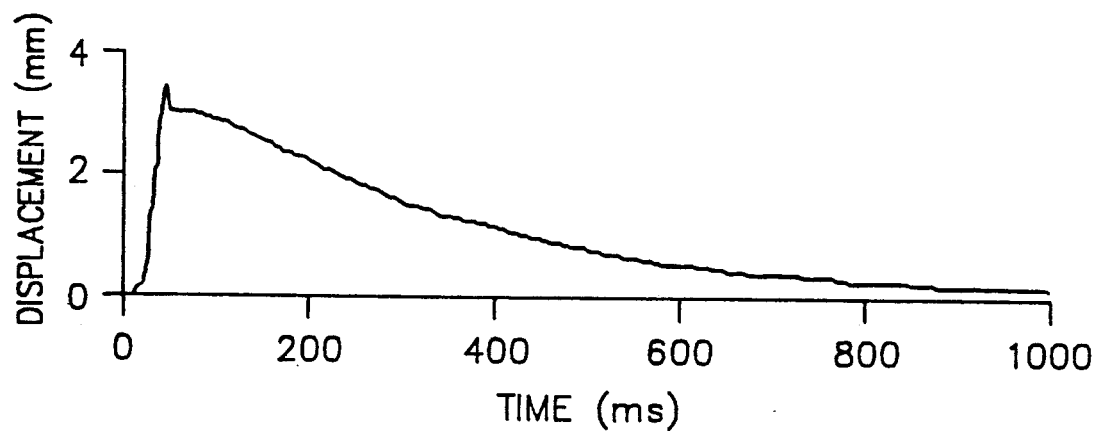
FIG. 1 illustrates graphically the twitch response of a prior art, unmodified shape memory alloy fiber.

With further reference to FIG. 1, there is illustrated the twitch response of a conventional Ni-Ti fiber 100 mm in length and 0.8 mm in diameter, heated by passing a pulse current through it of 50 amps for 1 ms. The heating causes the fiber to contract rapidly to the memory state with a displacement of about 3.5 mm in length in a contraction rise time of about 50 ms. The relaxation decay time by cooling after the heating has ceased is slow and is not complete even after 1000 ms.

Figure 2:
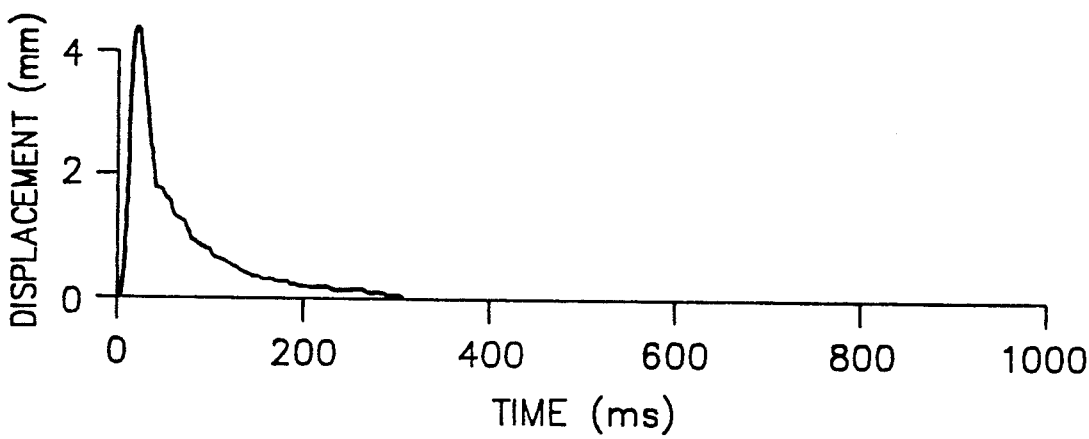
FIGS. 2 and 3 illustrate graphically the twitch response of a modified fiber of the invention.

With further reference to FIG. 2, results are shown for the fiber of FIG. 1, but after modification in accordance with the invention. The modified or altered fiber now has a much shorter twitch response time. As can be seen from FIGS. 2 and 3, the contraction rise time is not more than 10 ms, and the relaxation decay time is considerably shortened being about 60% completed in 15 ms which is markedly shorter than that of the unmodified fiber in FIG. 1.

Further it can be seen from FIG. 2 that the total relaxation decay time of the modified fiber is very much shorter than that of the unmodified fiber of FIG. 1. More especially the relaxation decay time of the modified fiber of FIG. 2, which relaxation decay time comprises a rapid relaxation followed by a slower relaxation, is complete in less than 400 ms, more especially about 300 ms and this is markedly shorter than the more than 1000 ms of the unmodified fiber of FIG. 1.

Figure 3:
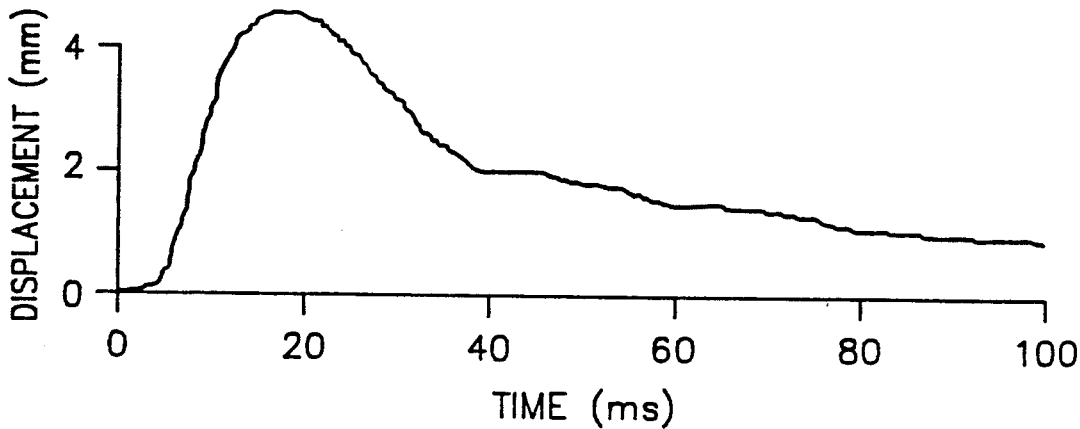

In reference to FIG. 3 it is clear that whilst the fiber relaxes by 60% very rapidly the final 40% is relatively slow and for this reason it is appropriate to constrict a motor unit with 5 to 15 preferably 10 fibers. Instead of activating all 10 fibers in the motor unit simultaneously it is appropriate to actuate them sequentially. Thus in the case of a motor unit of 10 fibers a given fibre is not activated again until 10 activation pulses later. Activation of a subsequent fiber will usually take place while the immediately preceding activated fiber is in the rapid phase of the relaxation.

Figure 4:
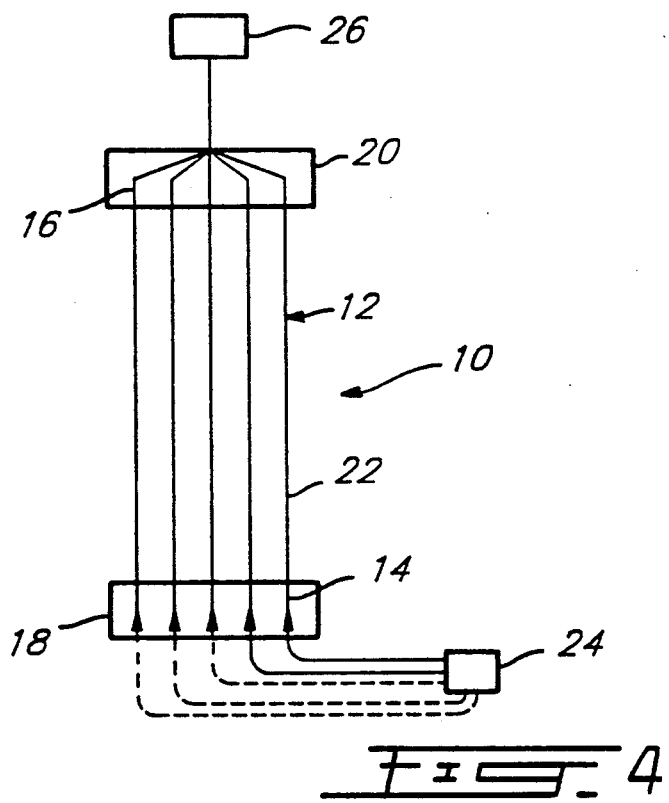
FIG. 4 illustrates schematically a motor unit of the invention in a first embodiment.

With further reference to FIG. 4, there is illustrated schematically a motor unit 10 for use in an artificial muscle (not shown). Motor unit 10 has a plurality of elongate modified fibers 12, of the invention, in generally parallel side-by-side relationship and having ends 14 and 16 supported in clamps 18 and 20 respectively.

The fibers 12 are insulated along their length by an electrically insulating coating 22.

The ends 14 are insulated from each other in clamp 18, whereas the ends 16 are in electrical contact with each other through clamp 20.

An electromagnetic source 24 provides an electromagnetic pulse to ends 14; the pulse may be applied to one or more of ends 14, sequentially or simultaneously depending on the work force required, as shown in the broken line.

The working force generated by the deformation of the fibers 12 to their memory state is communicated to work element 26.

Figure 5:
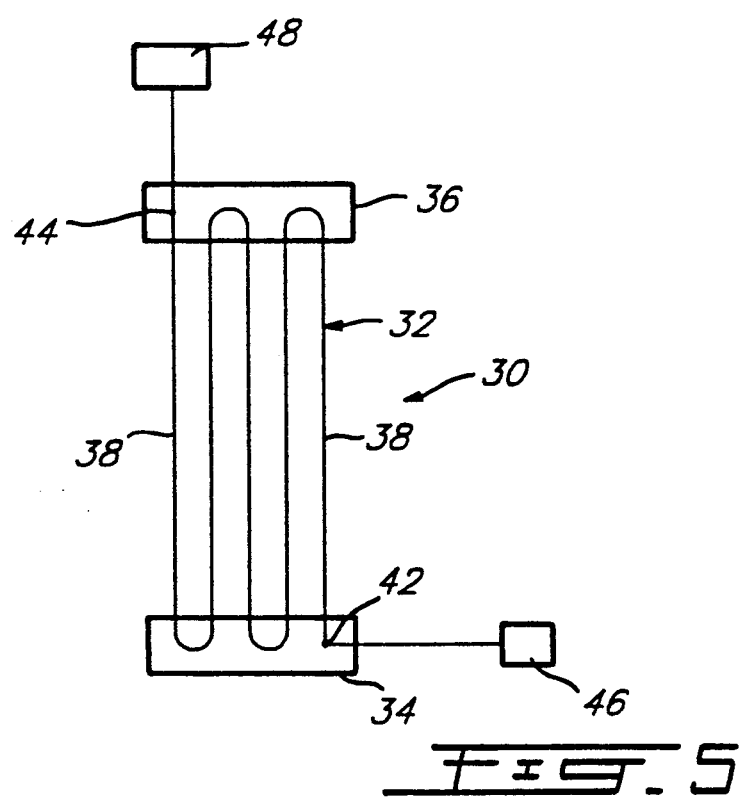
FIG. 5 illustrates schematically a motor unit of the invention in a second embodiment.

With further reference to FIG. 5, a motor unit 30 has a single elongate fiber 32 arranged in a sinusoidal like manner between opposed clamps 34 and 36, thereby providing a plurality of side-by-side lengths 38 of the fiber.

The fiber 32 is electrically insulated by an insulating coating 40, and has an input end 42 and an output end 44.

Input end is electrically connected to an electromagnetic source 46 and output end is connected to a work element 48.

Application of an electromagnetic pulse to fiber 32 from source 46 heats the fiber causing return to the memory state and the shape change force generated is communicated to work element 48.

A plurality of the motor units 10 or 30 may be arranged in parallel and employed sequentially. If a low working force is required only some of the motor units may be employed whereas if a high working force is required all of the motor units of the plurality may be employed. The motor units 10 and 30 of the invention permit considerable flexibility in the operation of a prosthesis or robotic.

This invention may be embodied in other forms or carried out in other ways without departing from the spirit or essential characteristics thereof. The present embodiments are therefore to be considered as in all respects illustrative and not restrictive, the scope of the invention being indicated by the appended claims, and all changes which come within the meaning and range of equivalency are intended to be embraced.

We claim:

1. An actuator element for generation of a working force comprising a modified elongate fiber of a shape memory alloy, said modified fiber being derived from an unmodified fiber, said unmodified fiber having been modified by being subjected a plurality of times to a short, very powerful electromagnetic pulse effective to cause contraction of the length of the unmodified fiber and change material properties while under a stretching force serving to elongate said length, said modified fiber exhibiting a twitch response under stimulation by an action potential, said twitch response comprising a contraction time and a relaxation time, said twitch response being rapid as compared with the twitch response of the unmodified fiber.

2. An actuator element according to claim 1, wherein said rapid twitch response is less than 40 ms when subjected to the action potential of an electromagnetic pulse.

3. An actuator element of claim 2, wherein said shape memory alloy is a Ni-Ti alloy and said fiber has a diameter of 0.01 to 10 mm.

4. An actuator element of claim 1, wherein said pulse has a current density of 400 to 4,000 MA/m$^2$.

5. An actuator element of claim 1, wherein said pulse has a rate of current change of at least 200,000 A/sec.

6. An actuator element of claim 1, wherein said pulse has a current density of 400 to 4,000 MA/m$^2$ and has a rate of current change of at least 200,000 A/sec.

7. An elongate fiber of a shape memory alloy modified by having been subjected a plurality of times to a short, powerful electromagnetic pulse effective to cause contraction of the length of the fiber and change material properties, while under a stretching force serving to elongate said length, wherein said pulse has a current density of 400 to 4000 MA/m$^2$, and has a rate of current change of at least 200,000 A/sec.

8. An elongate fiber of claim 7, wherein said shape memory alloy is a Ni-Ti alloy and said fiber exhibits a rapid twitch response having a total contraction and relaxation time of less than 40 ms when subjected to an action potential of an electromagnetic pulse effective to heat said fiber to the shape memory state.

9. An elongate fiber of claim 8, having a diameter of 0.01 to 10 mm.

10. A motor unit for generation of a working force in response to stimulation by an action potential in an artificial muscle comprising;
    first and second opposed, spaced apart clamping means,
    at least one elongate actuator element comprising an elongate fiber of a shape memory alloy providing a plurality of lengths of fiber in side-by-side, generally parallel relationship extending between said spaced apart clamping means, said lengths being electrically insulated from each other and from said first clamping means,
    electrical connection means for connecting said at least one fiber to a source of electromagnetic pulses at said first clamping means, and
    connection means at said second clamping means for connecting said at least one fiber to a work element,
    said elongate fiber exhibiting a twitch response under stimulation by an action potential, said twitch response comprising a contraction time and a relaxation time and being less than 40 ms.

11. A motor unit of claim 10, wherein said at least one elongate actuator element comprises a plurality of discrete actuator elements in generally parallel side-by-side relationship.

12. A motor unit of claim 10, wherein said at least one elongate actuator element comprises a single actuator element entrained in a generally sinusoidal manner between the clamping means.

13. A motor unit of claim 10, wherein said elongate actuator element is characterized by having been subjected a plurality of times to a short, powerful electromagnetic pulse effective to cause contraction and change material properties, while under a stretching force.

14. A motor unit of claim 13, wherein said pulse has a current density of 400 to 4,000 MA/m$^2$.

15. A motor unit of claim 13, wherein said pulse has a rate of current change of at least 200,000 A/sec.

16. A process for modifying an elongate fiber of a shape memory alloy comprising subjecting said elongate fiber to a stretching force while applying a plurality of short, very powerful electromagnetic pulses effective to cause contraction and change material properties of the fiber, wherein said electromagnetic pulses have a current density of 400 to 4000 MA/m$^2$.

17. A process according to claim 16, wherein said fiber is a Ni-Ti fiber having a diameter of 0.01 to 10 mm.

18. A process for modifying an elongate fiber of a shape memory alloy comprising subjecting said elongate fiber to a stretching force while applying a plurality of short, very powerful electromagnetic pulses effective to cause contraction and change material properties of the fiber, wherein said pulses have a rate of current change of at least 200,000 A/sec.

19. A motor unit of claim 18, wherein said pulses have has a current density of 400 to 4,000 MA/m$^2$.

20. A process for modifying an elongate fiber of a shape memory alloy comprising subjecting said elongate fiber to a stretching force serving to elongate the length of the fiber while applying a plurality of short, very powerful electromagnetic pulses effective to cause contraction and change material properties of the fiber, said fiber being a Ni-Ti fiber having a diameter of 0.01 to 10 mm, wherein said fiber prior to said subjecting has a twitch response comprising a total contraction rise time and relaxation decay time greater than 1000 ms, and said fiber after said subjecting has a twitch response of less than 40 ms.

21. A process according to claim 20, wherein said plurality is up to about 100.

22. A process according to claim 21, wherein said pulses have a rate of current change of at least 200,000 A/sec.

23. A modified elongate fiber derived from an elongate unmodified fiber of a shape memory Ni-Ti alloy, said unmodified elongate fiber having a twitch response, when subjected to an action potential effective to heat said fiber to the shape memory state, with a total contraction and relaxation time greater than 1000 ms, said modified fiber having a twitch response of less than 40 ms and said modified fiber having a diameter of 0.01 to 10 mm, said unmodified fiber having been modified by being subjected a plurality of times to a short, powerful electromagnetic pulse having a current density of 400 to 4,000 MA/m$^2$, and a rate of current change of at least 200,000 A/sec, effective to cause contraction of the length of the unmodified fiber and change material properties while under a stretching force serving to elongate said length.

* * * * *